United States Patent [19]
Greene et al.

[11] Patent Number: 5,123,410
[45] Date of Patent: Jun. 23, 1992

[54] TUBE CLAMP

[76] Inventors: Worthington W. Greene, 2984 Millcreek Rd., Salt Lake City, Utah 84109; Dennis J. Wyman, 242 E. Ensign Vista Dr., Salt Lake City, Utah 84103

[21] Appl. No.: 544,998

[22] Filed: Jun. 27, 1990

[51] Int. Cl.$^5$ .............................................. A61M 16/00
[52] U.S. Cl. ...................... 128/207.17; 128/DIG. 26
[58] Field of Search ..................... 24/463; 248/225.31, 248/230, 231.2; 128/DIG. 26, DIG. 26, 207.17

[56] References Cited

U.S. PATENT DOCUMENTS

| | | | |
|---|---|---|---|
| 1,502,890 | 7/1924 | Veasey | 24/463 |
| 1,969,831 | 8/1934 | Williams | 604/178 |
| 2,534,527 | 12/1950 | Myers | 24/463 |
| 2,606,792 | 8/1952 | Marsh | 24/463 |
| 2,775,869 | 1/1957 | Pointer | 24/463 |
| 2,820,457 | 1/1958 | Phillips | 128/200.26 |
| 3,821,957 | 7/1974 | Reily et al. | 604/178 |
| 3,844,002 | 10/1974 | Slemmons | 24/463 |
| 4,114,626 | 9/1978 | Beran | 604/180 |
| 4,657,283 | 4/1987 | White | 24/463 |
| 4,683,882 | 8/1987 | Laird | 128/207.17 |

*Primary Examiner*—Edgar S. Burr
*Assistant Examiner*—Aaron J. Lewis

*Attorney, Agent, or Firm*—Terry M. Crellin

[57] ABSTRACT

The present invention relates to a tube holder for securing a tube in fixed position relative to an object. The tube holder includes an annular collar having a central annular member, a pair of end pieces, and an inflation bladder. The inflation bladder is attached to the inner annular surface of the central annular member and secured thereto in air tight relationship by the end pieces. An inflation tube is passed through the central annular member so as to be in fluid flow relationship with the inflation bladder, with its opposite end being attached to a check valve. The tube holder is used by inserting a tube through the annular collar. When the inflation bladder is deflated, the tube will slide relative to the annular collar therefore allowing positioning thereof. When the desired position is achieved, the inflation bladder is inflated by attaching a syringe to the check valve and introducing fluid under pressure through the check valve and inflation tube into the collar member to form an inflated channel between the inflation bladder and the inner surface of the central annular member. The inflation bladder, when inflated, contacts and securely fixed the annular collar in position relative to the tube. If desired, the syringe can be used to withdraw fluid from the annular collar, thus allowing the tube to again be slidable relative thereto for repositioning.

4 Claims, 3 Drawing Sheets

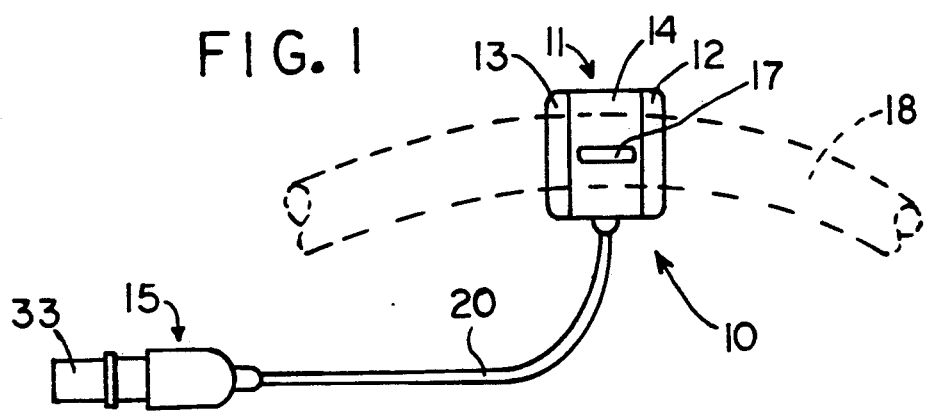
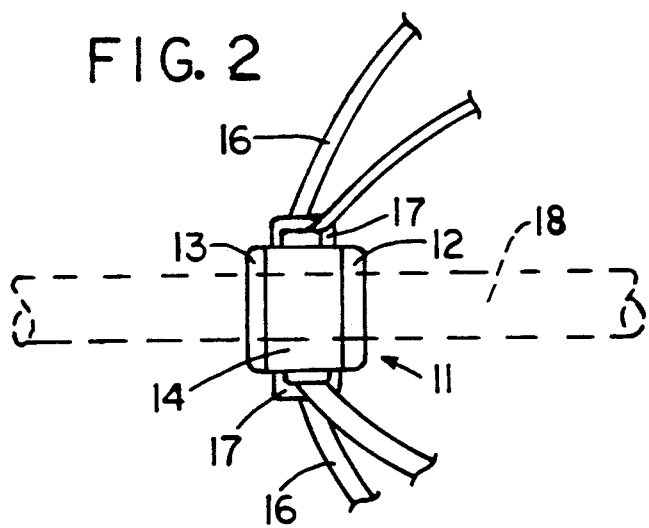
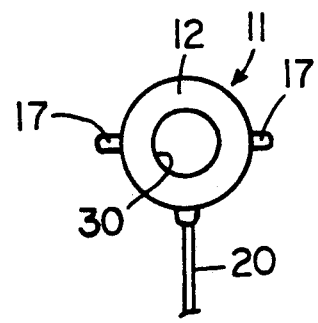
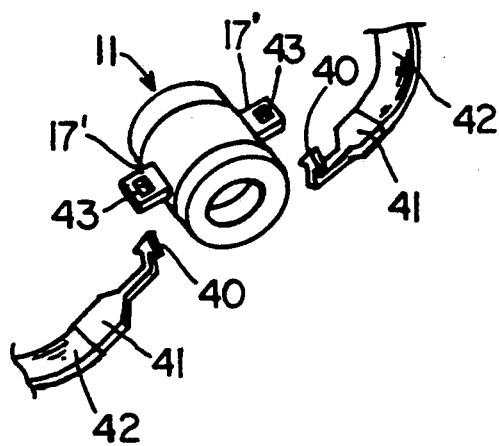

TUBE CLAMP

BACKGROUND OF THE INVENTION

1) Field of the Invention

The present invention relates generally to a clamp for immobilizing a tube. More specifically, the present invention relates to an inflatable clamp generally useful for holding a tube, such as a endotracheal tube or other medical tube, in a desired position relative to a patient's anatomy.

2) Prior Art

A number of procedures, particularly operations or other procedures performed on patients by medical personnel include the insertion of medical tubes into the patients body, either through natural openings or through incisions or the like. In most cases, such tubes must be secured to the patients body in order that they remain correctly positioned during their use.

For example, endotracheal tubes are frequently placed through the mouth or nose of a patient into the patients trachea in order to assist the patient in breathing. It is important that the endotracheal tube remain precisely as positioned throughout the entire time it is located in the patients trachea. If the endotracheal tube is not securely held in its proper position, and instead becomes dislodged, or displaced, it may result in respiratory arrest or aspiration of stomach contents into the patients lungs, or even move into the main stem bronchus of the patient resulting in only one lung being utilized for respiration. These tube displacements are obviously extremely dangerous to the patient.

Other tubes such as feeding tubes, ostomy tubes, and general catheterization tubes, may also become very dangerous to the patient if dislodged or improperly positioned.

It is therefore important to have a device which is capable of readily securing a tube to a patients anatomy once the tube is placed in its proper position in the patient to prevent dislodgement or displacement thereof.

There have been several prior art attempts to develope a device for securing a tube in position in a patients body. Several devices which are exemplary of these prior art attachment devices are disclosed in U.S. Pat. No. 2,820,457, to Phillips, U.S. Pat. No. 3,821,957 to Reily et al., U.S. Pat. No. 4,114,626 to Beran, and U.S. Pat. No. 4,683,882 to Laird. In each of each above noted patents, a tube such as an endotracheal tube, is held in position by a fastening device which is itself secured to the patients body. In each case however, the securing of the endotracheal tube to the patient involves a rather time consuming process for the medical personnel, including several attachment steps which are not easily reversible should it become necessary to reposition the tube, once it has been initially secured by the device. The time in which it takes medical personnel to reposition a tube in a patient's body can be extremely critical to the patient, especially in emergency type situations where speed can sometimes spell success or failure of the medical treatment being offered. Even at times when the patient will not be adversely affected by an extended process of removing a fastening device to reposition a tube, the medical personnel's time is nevertheless very valuable and could generally be better used to other purposes.

There is therefore a need in the art which the prior attachment devices have not successfully addressed. This need is for the development of a tube holding device, such as a tube clamp, which can be quickly and easily positioned on a tube for attaching it to a patients body. There is further a need such as a device which, once attached to a tube, can be very quickly and easily released therefrom (without the necessity of removing the clamping device from its attachment to the patients body) and rapidly readjusted to a new position on the tube, and then quickly resecured to the tube for immobilization thereof in its repositioned orientation.

OBJECTS AND SUMMARY OF THE INVENTION

It is an object of the present invention to provide a tube clamp which is easily movable up and down a tube in an infinite number of positions and is easily and quickly fixable to the tube in any desired position.

Another object of the present invention is to provide a tube clamp having a clamping mechanism which is quickly and easily actuated to clamp a tube therein, and which is also quickly and easily actuatable to unclamp the tube when desired. It is also an object of the present invention to provide a tube clamp as defined above which can be securely attached to a patient's body, and which can be quickly and easily adjusted along the tube without the necessity of removing it from its secure attachment to the patient's body.

It is further another object of the present invention to provide a tube clamp which is of an overall size which is not significantly larger than the tube itself therefore allowing, in the case of use of the tube clamp in conjunction with an endotracheal tube, medical personnel maximum room for the insertion of other medical instrumentation into the patients mouth without interference from the tube clamp.

These and other objects of the present invention are inherent in the below described embodiments thereof which include an annularly shaped collar which can be slid along a tube in an infinite number of positions, the collar including an inflatable bladder on the inner annular surface thereof which can be inflated or deflated to clamp or unclamp a tube at any position therealong, inserted through the annular opening of the device.

The inflatable collar comprises a central molded annular piece which has a cylindrically shaped interior surface over which an expandable bladder is placed. The ends of the expandable bladder extend from the ends of the cylindrical surface and are clamped in position at each end of the central annular piece by a pair of annular end pieces.

An inflation tube is attached through the annular outer surface of the collar so as to be in fluid flow relationship with a chamber between inflation bladder and the inner annular surface of the collar, the opposite end of the inflation tube being connected to a standard valve through which inflation fluid may be passed by an ordinary syringe. The exterior annular surface of the collar may also include D-rings attached thereto which can be used in conjunction with ties to secure the device to the patients body. If desired, the ties may work in conjunction with a trach tube to secure proper placement of the device relative to the trach tube. Also, if desired a bite guard may be formed in conjunction with the device.

The present invention is used by passing a tube through the annular opening of the inflatable collar prior to inserting the tube into the patient's body. Once the tube is correctly positioned in the patient's body, the annular collar can be affixed to the patient by the ties. The inflation member is then inflated by attaching a syringe to the check valve of the inflation tube and inserting fluid therethrough into the collar to fill a chamber between inflation bladder and the inner annular surface of the collar. If it is later desired to reposition the tube, the syringe is used to remove the fluid from the chamber and the tube is repositioned. The chamber is then refilled in the manner as described above.

BRIEF DESCRIPTION OF THE DRAWINGS

FIG. 1 shows a side view of a tube clamp made in accordance with the principles of the present invention;

FIG. 2 shows a top view of a tube clamp made in accordance with the principles of the present invention including tie members used to attach it to a patients body;

FIG. 3 shows a front view of the tube clamp made according to the principles of the present invention;

FIG. 8 shows a perspective view of the tube clamp of the present invention with an alternative embodiment of attachment ties;

DETAILED DESCRIPTION OF THE PRESENT INVENTION

Figure 4:
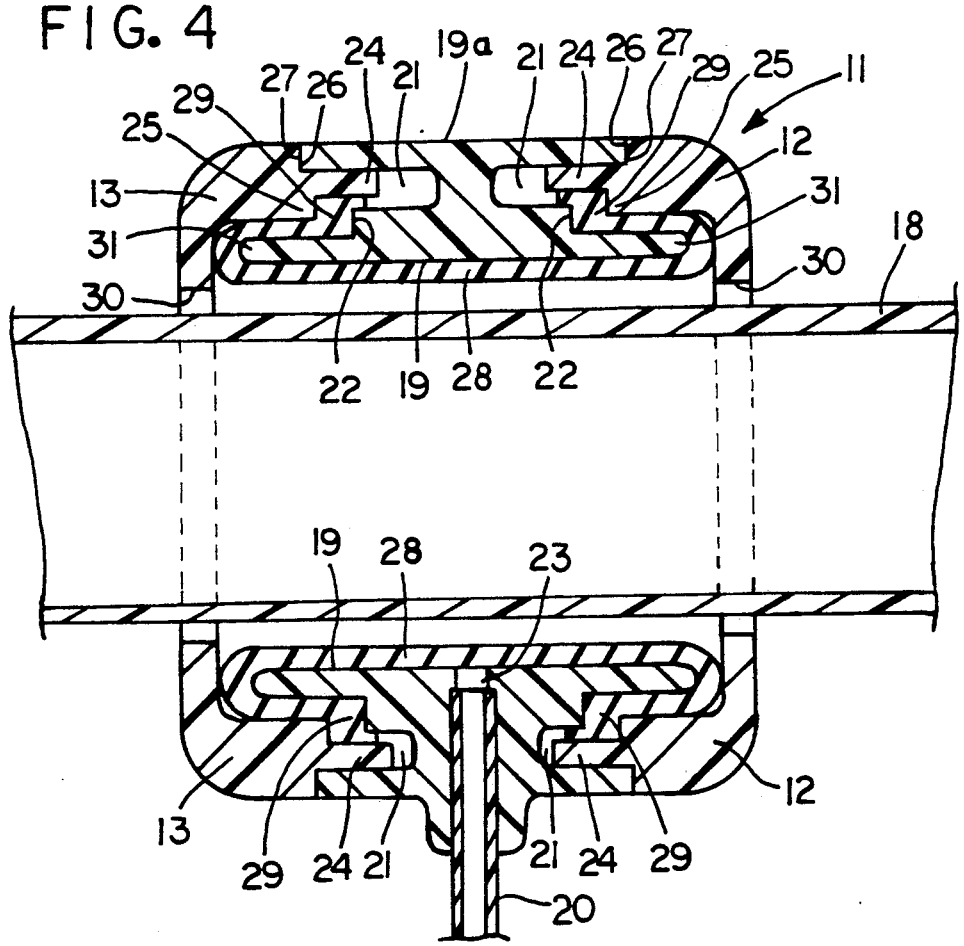
FIG. 4 shows a cross-sectional view of the tube clamp of the present invention taken along line IV—IV of FIG. 2.

As shown in FIGS. 1-3, the tube clamp 10 of the present invention includes an inflatable collar 11 which is attached to an inflation/deflation valve 15 through an inflation tube 20.

The inflation collar 11 includes a central annular member 14 which has a pair of annular end pieces 12 and 13 attached to each annular end thereof. The central annular member 14 also includes a plurality of D-ring type attachment members which allow for attachment of ties 16 (as shown in FIG. 2) for securing the clamp 10 to the patient's body. Central annular member 14 also has attached thereto inflation tube 20 as will be more clearly explained below.

As shown in dashed lines, tube 18 passes through the annular inflatable collar 11 along the central longitudinal axis thereof and is allowed to freely slide relative thereto while the collar 11 is in its deflated state.

As best seen in FIG. 4, which is a cross-sectional view of the inflatable collar 11, the central annular member 14 is generally cylindrical in shape having a smooth cylindrical inner surface 19, and a smooth cylindrical outer surface 19a. The annular ends of the central annular member 14 each are formed with annularly shaped, grooves 21 therein with each groove 21 having an annularly shaped shoulder portion 22 formed on the inner side thereof.

An inflation channel 23 extends radially inwardly through the central member 11, from the outer surface 19a to the inner surface 19 thereof. The inflation channel 23 is sized to allow inflation tube 20 to be inserted therein in a fluid tight manner. The inflation tube 20 can be fixed in inflation channel 23 by any prior art method such as a friction fit, solvent bond, etc.

Each of the annular end pieces 12 and 13 are identical. Each includes an annular tab 24 which is sized to be insertable into the annular grooves 21 of the central annular member 14. Further, each annular tab 24 includes an annular shoulder 25 and a stopping surface 26. When assembled, the stopping surfaces 26 abuts with the ends 27 of the outer surface 19a of the central annular member 14 in a fluid tight junction. The end pieces 12 and 13 are assembled onto central member 14 by inserting tabs 24 into grooves 21. Tabs 24 and/or stopping surfaces 26 and ends 27 may be held in their assembled orientation in any well known manner such as by friction fitting, solvent bonding or the like.

Annular end pieces 12 and 13 also include centrally located annular openings 30, the central axis of which corresponds to the central longitudinal axis of the inner cylindrical surface 19 of the central annular member 14. Thus, when assembled, a tube 18 may pass through the openings 30 along the longitudinal axis of the inner cylindrical surface 19 and be completely encircled by the body of inflatable collar 11. The central member 14 and the end pieces 12 and 13 can be formed of any well known material useful for such purposes including metal, polymeric material, or the like.

An inflatable bladder 28 is formed of a generally cylindrical shape having generally annular shoulders 29 formed at each end thereof. The inflatable bladder 28 can be formed of any material which will expand in a balloon fashion. Examples of such material would be rubber, latex, or other generally elastic polymeric materials.

The inflatable bladder 28 has an external diameter which is roughly equivalent to the internal diameter of the cylindrical inner surface 19 of the central annular member 14. The bladder 28 is inserted into the opening formed by the cylindrical inner surface 19 and generally centered therein so that the outer surface of the bladder 28 contacts the inner surface 19 of the central annular member 14, with the length of the bladder 28 being slightly greater than the length of the inner surface 19.

Once placed in this position, the shoulders 29 of the inflation bladder 28 are wrapped around the ends 31 of the cylindrical inner surface 19 abutted against shoulders 22 located in groves 21 of the central annular member 14. Annular end pieces 12 and 13 are then positioned about the central annular member 14 in such a manner that tabs 24 can be slid into groves 21. When the annular end pieces 12 and 13 are slid into their assembled position, shoulders 25 thereof contact and compress the shoulders 29 of the inflatable bladder 28 against the shoulder 22 of the central member 14. When annular end pieces 12 and 13 are completely slid to their assembled positions (where the stopping surfaces 26 thereof abut the ends 27 of the outer cylindrical surface 20 of the central annular member 14) the shoulders 29 of the inflatable bladder 28 are sufficiently compressed between shoulders 25 of the annular end pieces 12 and 13 and the shoulders 22 of the central annular member 14 that they become fixedly held in this assembled position in an air tight manner.

As shown in dashed lines, a tube 18 can be inserted through openings 30 of the end pieces 12 and 13 along the longitudinal axis of the central annular member 14. The tube 18 is allowed to slide freely relative to the inflatable collar 11 as long as the bladder 28 remains deflated.

Figure 5:
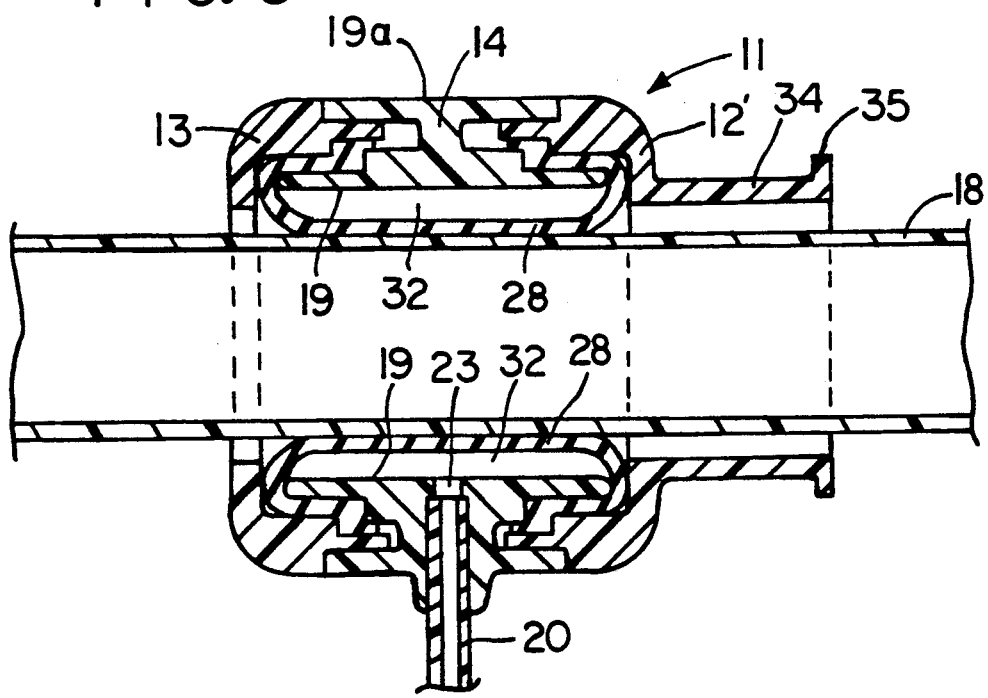
FIG. 5 is a cross-sectional view of an alternative embodiment of a tube clamp which is also made in accordance with the principles of the present invention.

FIG. 5 shows a cross-sectional view of the inflatable collar 11 of the present invention with a tube 18 passing centrally therethrough as has been described above with respect to FIG. 4. In FIG. 5 however, the inflation bladder 28 has been inflated in such a manner that it now contacts the external surface of the tube 18 and holds the collar 11 in fixed position relative thereto.

The bladder 28 is forced into contact with the tube 18 due to inflation fluid being forced through inflation tube 20 and against the bladder 28 to form a generally annular fluid filled chamber 32 between the inner cylindrical surface 19 and the bladder 28. Obviously, the gripping force exerted on tube 18 by bladder 28 will correspond to the pressure of fluid forced into chamber 32.

As best seen in FIG. 1, the inflation tube 20 is attached to a valve 15. The valve 15 is a common prior art valve which is used routinely for inflation of balloons associated with tubes and other well known types of medical devices. The valve 15 is readily connectable by means of a leur fitting 33 or other common type connection, to a standard syringe (see FIG. 6).

The valve 15 functions to allow fluid to pass thereto only under a predetermined pressure deferential. The syringe therefore is used to generate a high pressure which thus opens valve 15 and allows the fluid to pass through inflation tube 20 into chamber 32.

The syringe can also be used to remove fluid from chamber 32 by causing a vacuum therein which causes valve 15 to open and fluid to pass from chamber 32 through inflation tube 20 back into the syringe. This manner of inflation and deflation using a syringe and a valve such as valve 15 is very well known in the art. It is contemplated that any well known means of inflation or deflation of the bladder 28 of the present invention be used with the inflation collar 11 if so desired depending only on the particular purposes and uses for which the inflation collar 11 is to be employed.

Figure 6:
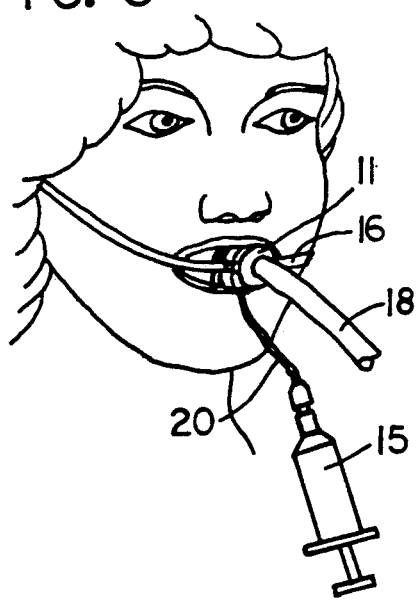
FIG. 6 shows the tube clamp of the present invention in use on a patient to hold a endotracheal tube.

FIG. 5 includes a modification to end piece 12. The end piece 12" as shown in FIG. 5 includes an extension 34 which is generally cylindrical in shape and which protrudes therefrom along the central longitudinal axis of the inflatable collar 11. The extension 34 is intended to be used as a bite guard in particular uses of the device 10 such as when being used to secure an endotracheal tube passing through the mouth of a patient. The extension 34 may include an annular lip 35 in order to provide the patient's bite from slipping from the end of the extension 34. When the collar 11 of the clamp 10 is located at the patient's mouth, extension 34 is inserted therein so that the teeth and lips of the patient rest thereon. It is to be understood that although extension 34 is used in conjunction with the tube clamp in the instance when the clamp 10 is used to hold an endotracheal tube in a patient's mouth, it is not necessary and is only intended to be disclosed as an optional feature of the present invention. Further, although the particular extension 34 shown in FIG. 5 has been described in conjunction with the clamp 10, it is contemplated that any well known design of bite guard used in conjunction with securing devices which secure a tube in position in a patient's mouth can be used, or adapted for use with the present invention, and any such use is specifically contemplated by this disclosure. As shown in FIG. 6, the clamp 10 of the present invention, when used to hold a tracheotomy tube in the mouth of a patient, does not entirely block the mouth opening as is the case with prior art clamping devices. The present invention is of a minimum over all size and is also specifically capable of being located in the patient's mouth in such a manner that other tools or instrumentation or the like which medical personnel must use or insert into the patient's mouth are allowed maximum space in the mouth opening. This becomes very important in the case of infants who must be attended to by medical personnel such as by placing instrumentation, medication, etc. into the infant's mouth while the clamping device is also located therein.

Figure 7:
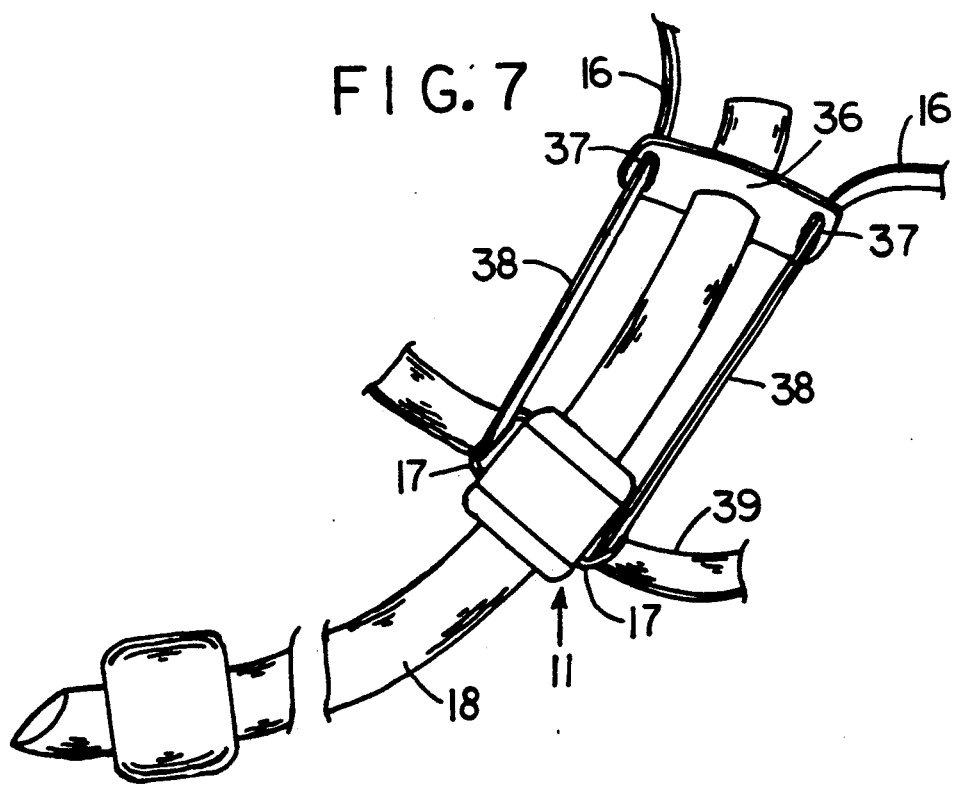
FIG. 7 shows the tube clamp of the present invention used in conjunction with a prior art type endotracheal tube.

FIG. 7 shows a particular use of the clamp 10 of the present invention on a prior art type tracheotomy tube. The clamp 10 is attached to a flange 36 by passing rigid members through openings 37 therein, thus allowing the clamp 10 to be slid along the tube 18 by pulling or pushing members 38 through openings 37. Once the inflatable collar 11 is inflated and fixed in position on tube 18, the ties 16 may then be used to secure the clamp 10 and the tube 18 directly to the patient's body. If desired, adhesive tapes 39 may also be used in conjunction with the collar 11 to aid in securing it to the patient's body.

FIG. 8 shows an alternative embodiment of the inflation collar 11 which includes a modification to the attachment members therefor. Specifically, attachment members 17' are formed with openings 43 therein which are sized to allow arrow shaped connectors 40 to pass therethrough. Once the connectors 40 are inserted through openings 43, they "snap in" to a locked position where they can no longer be removed. The connectors 40 are integrally formed with plastic tie 41 to which an adhesive strip 42 may be attached.

As is evident, the embodiment of FIG. 8 is used by snapping connector 40 through opening 43 and then securing the adhesive member 42 to the user's body.

Figure 9A:
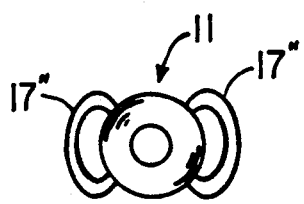
FIG. 9(a) shows a front view of the tube clamp of the present invention with an alternative embodiment of the attachment loops.
Figure 9B:
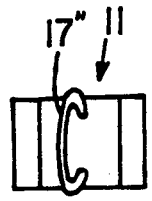
FIG. 9(b) shows a side view of the tube clamp of FIG. 9(a).

As is shown in FIG. 9(a) and 9(b), the collar 11 may also be fitted with another alternative attachment member. Attachment rings 17" are significantly larger than their counterparts on previous embodiments. The rings 17' are arcuate in shape and are attached to the collar 11 so as to extend in a radial direction around the collar 11 as opposed to previous embodiments, such as that shown in FIGS. 1-3, where the D-ring 17 is attached in a longitudinal manner along the collar 11.

Further, ring 17" is curved in shape along its own longitudinal axis instead of linear as shown in the previous embodiments.

Although in each of the shown embodiments, the element 17 is shown to be located in two radially opposed locations around the collar 11, it is anticipated and therefore felt to be well within the scope of the present invention, that attachment member 17 be attached around collar 11 at any location. Further, any desired number of attachment members 17 may be used.

It is also contemplated that any number of adhesive members may be used in conjunction with the ties 16 in order to securely attach the collar 11 to the user's body. A plurality of adhesive members may be attached directly over ties 16 to secure them to the user's body, or may be attached about the collar 11 or tube 18 in a manner such as is well known presently in the art, to insure secure attachment of the collar 11 to the user's body. Any combination of ties 16, adhesive members 42, or other types of securing devices are contemplated to be used in conjunction with the present invention to secure collar 11 in a fixed position relative to the user's body.

It is to be understood that the above described arrangements and embodiments are only illustrative of the application of the principles of the present invention. Numerous modifications and alternative arrangements may be devised by those skilled in the art without departing from the spirit and scope of the present invention and the appended claims are intended to cover such modifications and arrangements.

We claim:

1. A tube clamp which can be used to hold a tube in fixed relationship to a part of a patient's anatomy, said tube clamp comprising:
   an annular member forming a cylindrical outer surface, a cylindrical inner surface and a pair of opposite annular ends;
   a cylindrical bladder having opposite ends and an outer surface that lies adjacent to the inner surface of the annular member, with the opposite ends of the cylindrical bladder being turned outwardly and backwardly about the respective opposite annular ends of the annular member;
   a pair of annular end pieces attached to the annular member to secure the turned back ends of said cylindrical bladder in air tight relationship with said inner cylindrical surface of said annular member to form an inflation chamber between the inner surface of said annular member and the outer surface of said cylindrical bladder;
   inflation means for inflating and deflating said inflation chamber; and
   attaching means for attaching said clamp to said patient's anatomy,
   whereby a tube can be received through said annular end pieces and said cylindrical bladder to be (a) held in fixed relationship to said clamp and thus to the patient's anatomy when the inflation chamber is inflated and (b) released from said fixed relationship when the inflation chamber is deflated.

2. A tube clamp according to claim 1 wherein said inflation means includes
   a passageway extending radially inwardly through said annular member from said outer surface thereof to said inner surface thereof;
   an inflation tube attached to said passage; and
   a valve member attached to said inflation tube, said valve member controlling the flow of inflation fluid into and out of said inflation chamber through said inflation tube.

3. An endotracheal tube clamp which can be used to hold an endotracheal tube fixed to a patient's mouth and face, said endotracheal tube clamp comprising:
   an annular member forming a cylindrical outer surface, a cylindrical inner surface and a pair of opposite annular ends;
   a cylindrical bladder having opposite ends and an outer surface that lies adjacent to the inner surface of the annular member, with the opposite ends of the cylindrical bladder being turned outwardly and backwardly about the respective opposite annular ends of the annular member;
   a pair of annular end pieces attached to the annular member to secure the turned back ends of said cylindrical bladder in air tight relationship with said inner cylindrical surface of said annular member to form an inflation chamber between the inner surface of said annular member and the outer surface of said cylindrical bladder;
   inflation means for inflating and deflating said inflation chamber; and
   attaching means for attaching said clamp to said patient's mouth and face,
   whereby an endotracheal tube can be received through said annular end pieces and said cylindrical bladder to be (a) held in fixed relationship to said clamp and thus to the patient's mouth and face when the inflation chamber is inflated and (b) can be released from said fixed relationship when the inflation chamber is deflated.

4. An endotracheal tube clamp according to claim 3 wherein said inflation means includes
   a passageway extending radially inwardly through said annular member from said outer surface thereof to said inner surface thereof;
   an inflation tube attached to said passageway; and
   a valve member attached to said inflation tube, said valve member controlling the flow of inflation fluid into and out of said inflation chamber through said inflation tube.

* * * * *